United States Patent [19]
Wilks, Jr.

[11] Patent Number: 5,452,083
[45] Date of Patent: Sep. 19, 1995

[54] MULTIPLE INTERNAL REFLECTION OPTICAL ANALYZERS NOT REQUIRING EXTERNAL OPTICS

[76] Inventor: Paul A. Wilks, Jr., 179 Middlesex Rd., Darien, Conn. 06820

[21] Appl. No.: 233,361

[22] Filed: Apr. 25, 1994

[51] Int. Cl.[6] .............................................. G01N 21/27
[52] U.S. Cl. .................................... 356/300; 356/416; 356/246; 250/339.12; 250/341.1; 250/341.8
[58] Field of Search ............... 356/300, 416, 419, 244, 356/246, 445; 250/339.11, 341.1, 339.12, 341.8; 385/12

[56] References Cited

U.S. PATENT DOCUMENTS 3,998,591 12/1976 Eckfeldt ........................... 356/445
4,595,833  6/1986 Sting ................................. 356/300

FOREIGN PATENT DOCUMENTS 3-291551 12/1991 Japan ................................. 356/445

*Primary Examiner*—F. L. Evans

[57] ABSTRACT

Multiple internal reflection, MIR, rods or internal reflection elements, IRE, use the principal of frustrated total internal reflection, FTIR, (also known as attenuated total reflection, ATR,) in infrared spectroscopy, spectrometers, and spectrophotometers. The rods have their ends hollowed out to form a cone or wedge. A light source is located on the axis of a rod at the intersection of the perpendicular bisectors of the legs of the angle forming the cone or the faces of the wedge. Detectors are located at the intersection of these bisectors or centered on them closer to the hollowed out surfaces. The light source, under certain conditions, and the detectors may be located within the hollowed out portions. An analyzer for carbon dioxide ($CO_2$) content of beverages is disclosed in detail.

20 Claims, 3 Drawing Sheets

MULTIPLE INTERNAL REFLECTION OPTICAL ANALYZERS NOT REQUIRING EXTERNAL OPTICS

TECHNICAL FIELD

This invention relates to MULTIPLE INTERNAL REFLECTION OPTICAL ANALYZERS utilizing internal reflection elements providing multiple internal reflection, frustrated total internal reflection, and attenuated total reflection. The invention further relates to infrared spectroscopy, spectrometers, and spectrophotometers. Optical analyzers according to the invention are particularly useful for analyzing fluids, particularly liquids; for example, the carbon dioxide, $CO_2$ content in carbonated water and carbonated beverages.

BACKGROUND ART

Optical analyzers utilizing attenuated total internal reflection are disclosed in my earlier U.S. Pat. No. 3,460,893, Issued Aug. 12, 1969 for APPARATUS FOR ANALYZING A CONTINUOUS MOVING STRIP BY MEANS OF ATTENUATED TOTAL REFLECTION, my United Kingdom Patent No. GB 2,105,058B, Patent published Jan. 8, 1986 entitled FRUSTRATED MULTIPLE TOTAL INTERNAL REFLECTION ABSORPTION SPECTROPHOTOMETER, and my U.S. Pat. No. 5,185,640, Issued Feb. 9, 1993 entitled MULTIFACETED PROBES FOR OPTICAL ANALYSIS which patents are incorporated herein by reference. Each of the above patents discloses internal reflection rods for optical analysis. In the British Patent and the latter United States Patent the rods are utilized for analyzing fluids, particularly liquids.

All of these elements and all of the similar elements utilized in the prior art, I believe, have required the use of optical elements, such as lenses or reflecting mirrors to concentrate light from a light source into the elements and to collect the light exiting the elements and direct it to a detector.

Such light concentrating and light collecting optical elements add to the cost of any analyzer using totally internally reflecting rods according to the prior art.

A need exists in the beverage dispensing industry for an inexpensive monitor of the carbon dioxide ($CO_2$) content of carbonated water, for example, as supplied to the multiple soft drink dispensers used in restaurants and bars. The variation in $CO_2$ content is one of the main causes of improper taste in soft drinks.

DISCLOSURE OF THE INVENTION

This invention is an improvement over prior art optical analyzers utilizing totally internally reflecting rods, in that, it dispenses with optical elements for concentrating light from a source on to the rod and for gathering the light from the rod and directing it to one or more detectors.

The invention makes use of an infrared transmitting internal reflection rod having polished concave ends which may be wedges with parallel apexes intersecting the optical axis of the rod, or may be cones with the axes of the cones coincident with the optical axis of the rod, or may have a wedge at one end and a cone at the other. The angle of the wedge or the apex of the cone is slightly greater than twice the critical angle of incidence of the wavelengths to be used for optical analysis incident on the inner surface of said rod when immersed in a material to be analyzed.

The light source of the invention is a small nichrome wire mounted on a heat sink, such as diamond, located on the optical axis of the rod and at the intersection of the perpendicular bisectors of the wedge surfaces or the legs of the angle formed by the cone and a plane coincident with the optical axis. Thus, if the apex angle of the cone or wedge is less than 90° (as with a cubic zirconia rod), the infrared source will be located within the concave end of the rod.

Similarly, one or more small detectors may be located in the same position at the opposite end of the rod. A single detector is located at the intersection of the two bisectors, similar to the signal source. Dual detectors may each be located on a bisector facing opposite sides of the wedge or cone.

Filters may be placed directly on the end surfaces where the detector or detectors are located. A wedge shaped end is particularly useful for dual detectors, as different filter elements may be mounted on each wedge face and the detectors mounted on the filter elements or located at the previous described positions.

The material to be analyzed is in optical contact with the surface of the rod, such that total internal reflection takes place in the rod an evanescent wave passes slightly into the material to be analyzed, as is well known in the art.

The invention will be described, with particular reference to fluid analysis, particularly the analysis of the $CO_2$ content of water or carbonated beverages.

OBJECTS OF THE INVENTION

It is therefore an object of the invention to provide totally internally reflecting rods for optical analysis that do not require concentrating or collecting optics.

Another object of the invention is to provide optical analyzers utilizing only a single wavelength for analysis.

A further object of the invention is to provide for the efficient transmission of energy into and out of such rods.

Other objects of the invention will in part be obvious and will in part appear hereinafter.

The invention accordingly comprises the features of construction, elements, and arrangement of parts, which will be exemplified in the constructions herein set forth. The scope of the invention is indicated in the claims.

BRIEF DESCRIPTION OF THE DRAWINGS

For a fuller understanding of the nature and objects of the invention, reference should be had to the following detailed description, taken in connection with the accompanying drawings, in which.

The same reference characters refer to the same elements throughout the several views of the drawings.

BEST MODE FOR CARRYING OUT THE INVENTION

Figure 1:
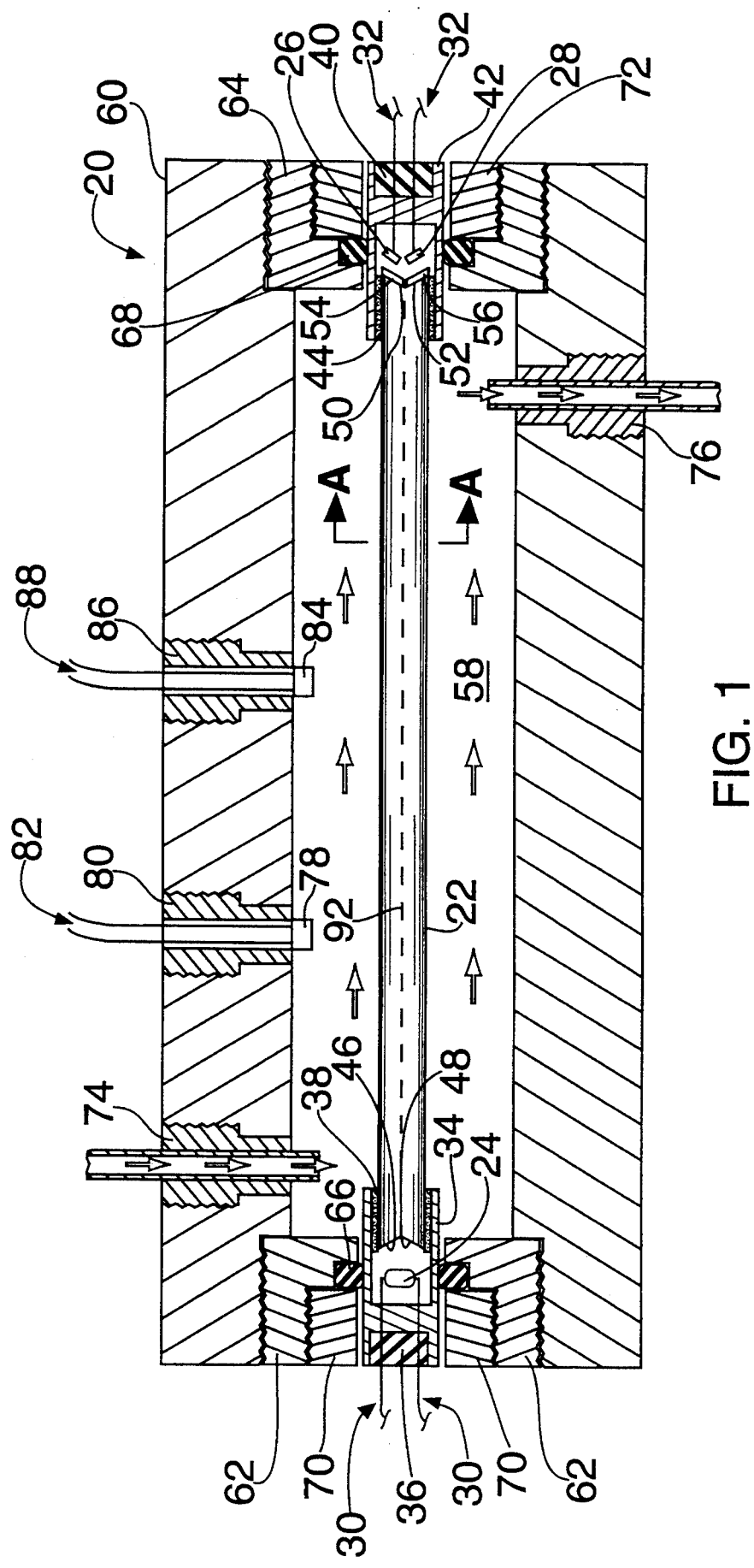
FIG. 1 is a cross-sectional view of a multiple internal reflection optical analyzer according to the invention for measuring a characteristic of a fluid.

Now referring to FIG. 1, a liquid analyzer according to the invention is generally indicated at 20. It comprises totally internally reflecting rod 22 which is transmissive at the wavelengths being used to analyze the liquid. An infrared light source 24 is located at one end of the rod 22 and a pair of detectors 26 and 28 at the other end. The light source 24 may be a nichrome wire mounted on a highly conductive heat sink such as diamond and is heated by means of electricity supplied on wires 30. The detectors 26 and 28 provide signals on wires generally indicated at 32.

The light source 24 is mounted within a capsule or end cap 34 which may be of metal or glass and is mounted in an insulator 36 at the end of the end cap. The end cap 34 is adhered to the rod 32 by an appropriate glass to glass or glass to metal seal 38.

Figure 2:
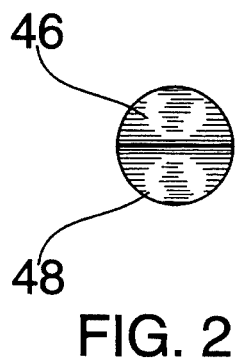
FIG. 2 is an left end view of the multiple internal reflection rod shown in FIG. 1.
Figure 3:
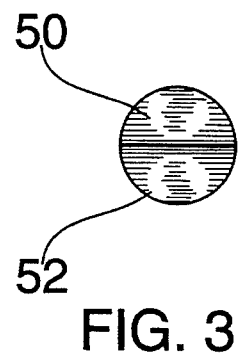
FIG. 3 is a right end view of the rod shown in FIG. 1.

Similarly, the detectors 26 and 28 are mounted to an insulator 40 in an end cap 42 which is sealed to the rod 22 by an appropriate sealant 44. The ends of the rods 22 are hollowed out by lapping to form wedge faces 46 and 48 on the left end thereof and wedge faces 50 and 52 on the right hand thereof (see FIGS. 2 and 3). Filters 54 and 56 are mounted to faces 50 and 52, respectively. Filters 54 and 56 are narrow band pass optical filters, one of which passes the analytical wavelength, and the other the reference wavelength as is well known in the art.

Rod 22 is mounted within a cylindrical chamber 58 within a block of metal 60. "O" ring mounts 62 and 64 are threaded into the block 60 and a pair resilent "O" rings 66 and 68. Sealing plugs 70 and 72 are threaded into "O" ring mounts 62 and 64, respectively, and the "O" rings seal around end caps 34 and 42 (as shown) or the rod 22. The fluid to be analyzed enters through supply pipe fitting 74 and exits through exit pipe fitting 76, as shown by the arrows. A temperature sensor 78 is mounted in temperature sensor plug 80 and supplies a temperature reading on electrical wires generally indicated at 82 and a pressure sensor 84 is mounted on pressure sensor plug 86 and provides a pressure reading on electrical wires generally indicated at 88.

It should be noted that the detectors 26 and 28 are mounted so that they face the opposite end faces 50 and 52 through the filters 54 and 56.

When the fluid to be analzyed is a carbonated beverage or carbonated water, the rod 22 may be cubic zirconia, preferrably, (or alternatively sapphire) coated with silicone oxide or diamond prevent the formation of bubbles on the surface of the rod 22.

Figure 4:
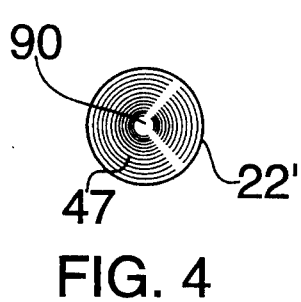
FIG. 4 is a left end view of an alternative embodiment of the rod shown in FIG. 1.
Figure 5:
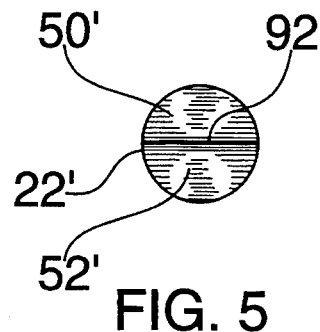
FIG. 5 is a right end view of the alternative embodiment of FIG. 4.

In an alternative embodiment of the invention, the left end of rod 22 may be in the form of a concave cone as shown in FIG. 4 and the right end may be wedge shaped as shown in FIG. 5. Thus, as shown in FIG. 4, the alternative rod 22' is formed with a conical concave surface 47 having an apex 90 located on the optical or central axis of symmetry of the rod 22 while the right end, as shown in FIG. 5, is wedge shaped with surfaces 50' and 52' forming the wedge with an apex 92 coincident with the optical axis or axis of symmetry 92.

The light source 24 is preferably not modulated, but is supplied with carefully controlled current and voltage on wires 30 to provide a constant output of infrared light. The detectors 26 and 28 may then be operated in the DC mode utilizing compensated detectors, such as are available from New England Photo-Conductor in Norton, Mass. Alternatively, the light source 24 may be modulated and the signals from the detectors 26 and 28 demodulated and processed as disclosed in my earlier above-identified U.S. Pat. No. 5,185,640. The rod 22 may be of the order of 0.5 centimeter in diameter and approximately 7.5 centimeters in length in which case the detectors 26 and 28 are approximately 1 milimeter square.

For measuring carbon dioxide, the reference wavelength may be 4.2 micrometers and the analytical wavelength 4.27 micrometers.

Figure 6:
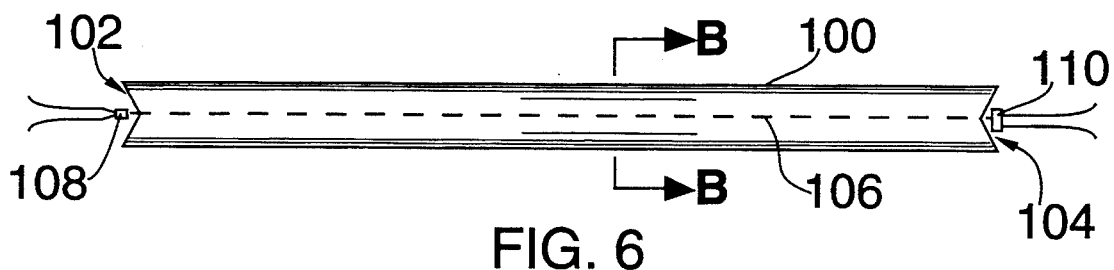
FIG. 6 is a diagrammatic view of another alternative embodiment of the invention.
Figure 7:
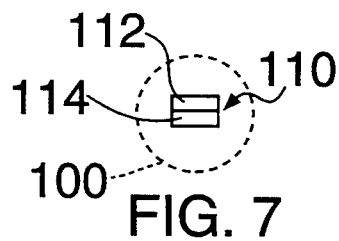
FIG. 7 is a left end view of the detector shown in FIG. 6; looking to the right in FIG. 6.
Figure 8:
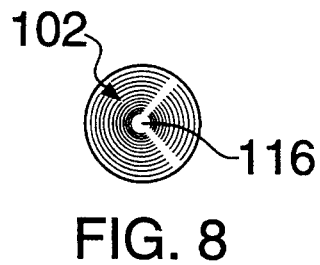
FIG. 8 is a left end view of the rod of FIG. 6.
Figure 9:
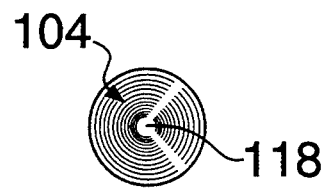
FIG. 9 is a right end view of the rod of FIG. 6.

FIG. 6 illustrates an alternative embodiment of the invention wherein an internally reflecting rod 100 having concave ends generally indicated at 102 and 104 and a axis of symmetry or optical axis 106 has a light source generally indicated at 108 mounted to illuminate the concave surfaces 102 and a detector 110 mounted on the axis 106 which as shown in FIG. 7 comprises an analytical detector 112 and a reference detector 114. As indicated in FIGS. 8 and 9, the ends 102 and 104 may, in this case, both be conical with their apexes 116 and 118 located on the axis 104.

Figure 10:
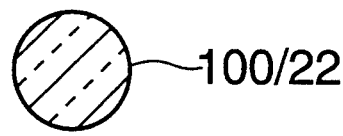
FIG. 10 is a cross-sectional view of the rods of FIGS. 1 and 6 taken along the lines A—A and B—B when they are right circular cylinders.
Figure 11:
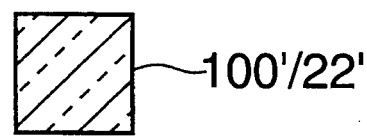
FIG. 11 is a cross-sectional view taken along the lines A—A and B—B of FIGS. 1 and 6 of an alternative embodiment of the rods in FIGS. 1 and 6 when they have a square cross section.

The rods 22 and 100 are preferably right circular cylinders as illustrated in FIGS. 2 through 5, 8 and 9 and having a circular cross-section at plane A—A in FIG. 1 or plane B—B in FIG. 6, as illustrated in FIG. 10. This is because they are easy to seal with the "O" rings 66, 68. However, other shapes may be employed. For example, the cross-sections A—A and B—B may be square as indicated in FIG. 11 in which case the wedge apex 92 shown in FIG. 5 would horizontally bisect the square cross-section shown in FIG. 11 or the conical apex would be in the center thereof.

Figure 12:
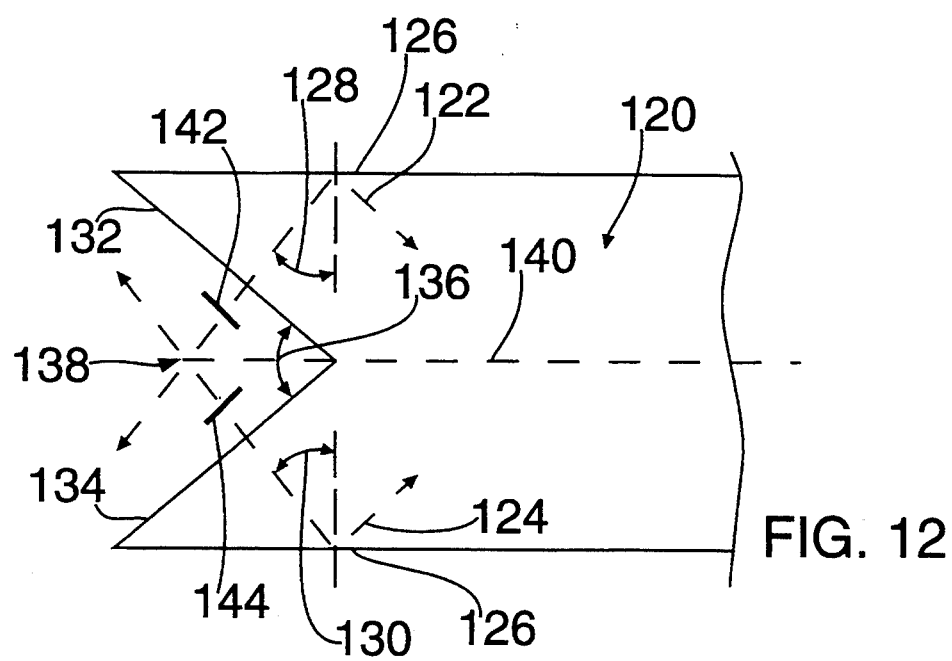
FIG. 12 is a diagrammatic cross-sectional view of an end of a multiple internally reflecting rod according to the invention.
Figure 13:
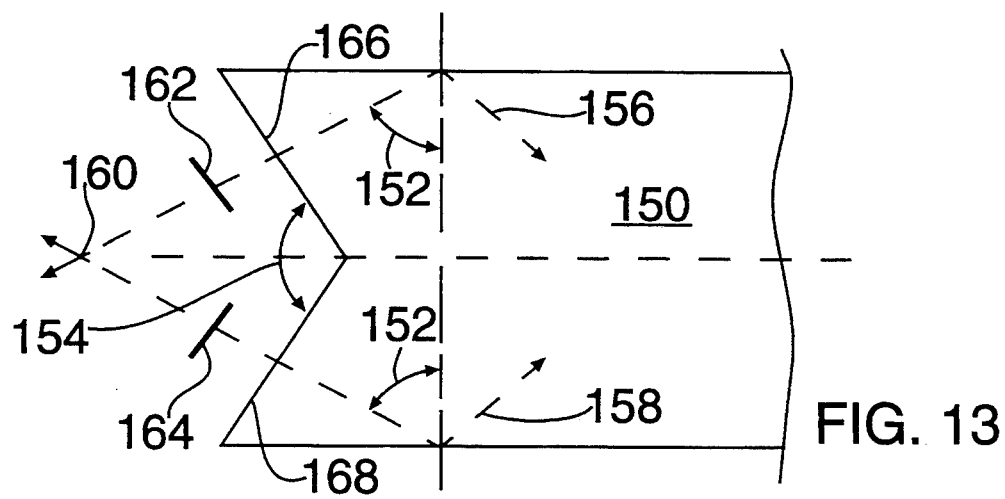
FIG. 13 is a diagrammatic view, similar to FIG. 12, of an alternative rod.

The geometry of the ends of the rods of my invention are illustrated in FIGS. 12 and 13. In FIG. 12, the material of rod 120 and the material to be analyzed cause the critical angle to be some what less than 45°. Thus, the angle at which light rays indicated at 122 and 124 must be incident on the surface 126 of the rod is less than 45° as indicated at 128 and 130. This angle is slightly greater than the critical angle, but must be fairly close to the critical angle as the magnitude of the evanescent wave decreases as the angle of incidence increases. Since the light rays 122 and 124 should penetrate the surfaces 132 and 134, perpendicularly to provide the greatest transmission, from geometry it will be seen that the apex angle 136 is twice the desired angle of incidence 128 and 130 and the rays 122 and 124 cross at a position 138 on the optical axis 140 within the wedge or cone formed by the surfaces 132 and 134.

Thus, with the desired angle of incidence 128 and 130 is less than 45°, the most desired position for the light source is at 138 where the light rays bisect the legs or faces 132 and 134 of the angle forming the wedge or cone, so that the maximum amount of light will be transmitted at the appropriate angle into the rod 120. Similarly, a single detector as illustrated at 110 in FIGS. 6 and 7, would also be located at position 138 in this situation. Dual detectors are mounted such that one faces face 132 and is centered on perpendicular bisector shown by ray 122 and the other faces face 134 on the perpendicular bisector shown by ray 124. Thus, one detector might be located at position indicated by the line 142 and the other indicated by line 144. In this case, both the detectors and the light source are mounted within the concave ends of the rod 120.

FIG. 13 illustrates the situation where the material of a rod 150 and the nature of the material in which it is immersed causes the desired angle of incidence 152 which is slightly above the critical angle to be greater than 45°. In this case, the apex angle 154 being twice the angle 152 is oblique and the central rays 156 and 158 cross at a position 160 which is outside of the concavity forming the angle 154. The light source would preferably be mounted at position 160 and again the detectors indicated at 162 and 164 would be located along the perpendicular bisector of the legs 166 and 168, respectively. Thus, the source is mounted outside the concave end and the detectors may be mounted inside or outside the concave end.

Figure 14:
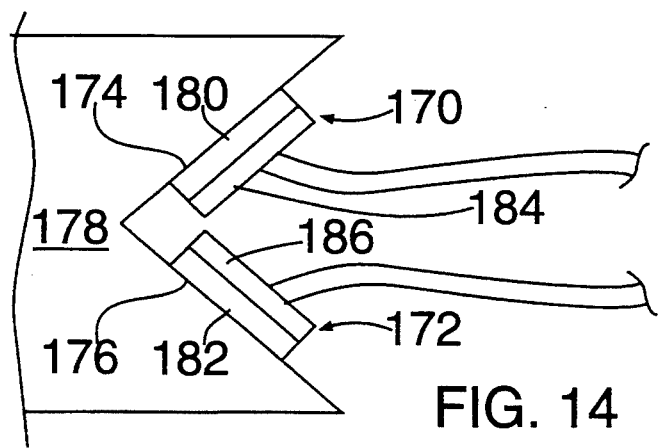
FIG. 14 is a diagrammatic view of an alternative placement of the detectors with respect to a multiple internally reflecting rod as shown in FIG. 1.

FIG. 14 illustrates another alternative embodiment of the invention wherein a pair of detectors generally indicated at 170 and 172 are mounted directly to the end faces 174 and 176 of a rod 178. These detectors have filters 180 and 182 which overlie their active elements 184 and 186.

It will thus be seen that the objects set forth above, among those made apparent from the preceding description, are efficently attained and, since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Having described my invention what I claim as new and desire to secure by Letters Patent is:

1. An optical analyzer comprising:
   A) a first electroptical transducer;
   B) a second electroptical transducer, one of said transducers being a source and the other being a detector of a wavelength of light to be used for optical analysis of a material; and,
   C) a cylindrical rod adapted for immersion in the material to be analyzed having a first and a second end, a cylindrical surface therebetween, and a centrally disposed axis of symmetry intersecting said ends, said first end of said rod being hollowed out to form an end surface which forms an angle having a first pair of legs at the intersection thereof with a plane coincident with said axis, said angle being slightly greater than twice the critical angle of incidence at said cylindrical surface of said rod when immersed in the material to be analyzed at said wavelength, said first transducer being located substantially on a perpendicular bisector of one of said legs, and said second transducer being located at the other end of said rod.

2. The analyzer defined in claim 1 wherein said first end of said rod is substantially conical.

3. The analyzer defined in claim 2 wherein said rod is a right circular cylinder.

4. The analyzer defined in claim 1 wherein said first end of said rod is substantially wedge shaped having two surfaces meeting at an angle.

5. The analyzer defined in claim 4 wherein said rod is a right circular cylinder.

6. The analyzer defined in claim 4; and,
   D) a third electroptical transducer located substantially on a perpendicular bisector of the other of said end surfaces forming said wedge, and wherein said first and third transducers are detectors of light and said second transducer is a light source.

7. The analyzer defined in claim 6 wherein said rod is a right circular cylinder.

8. The analyzer defined in claim 6; and,
   E) an optical filter on each of said surfaces forming said wedge.

9. The analyzer defined in claim 4; and,
   D) an optical filter on said one of said end surfaces.

10. The analyzer defined in claim 1 wherein said second end of said rod is hollowed out to form a second end surface which forms an angle having a second pair of legs at the intersection thereof with a plane coincident with said axis, said angle being slightly greater than twice the critical angle of incidence at said cylindrical surface of said rod when immersed in the material to be analyzed at said wavelength and said second transducer being a light source located substantially at the intersection of the perpendicular bisectors of said second pair of legs.

11. The analyzer defined in claim 6 wherein said second end of said rod is substantially conical.

12. The analyzer defined in claim 6 wherein said first and second ends of said rod are both substantially wedge shaped.

13. The analyzer defined in claim 6 wherein the first end of said rod is wedge shaped and the second end of said rod is a conical surface.

14. The analyzer defined in claim 13 wherein said transducers are located within said hollowed out portions of said ends of said rod.

15. An optical analyzer comprising:
   A) a first electroptical transducer;
   B) a second electroptical transducer, one of said transducers being a source and the other being a detector of a wavelength of light to be used for optical analysis of a material; and,
   C) a cylindrical rod adapted for immersion in the material to be analyzed having a first and a second end and a centrally disposed axis of symmetry intersecting said ends, said first end of said rod having a hollowed out portion, said first transducer being located substantially within said first end of said rod in said hollowed out portion, and said second transducer being located at the other end of said rod.

16. The analyzer defined in claim 15 wherein said first transducer is a light source.

17. The analyzer defined in claim 15 wherein said first transducer is a light detector.

18. The analyzer defined in claim 15 wherein said second end has a hollowed out portion and said second transducer is located substantially within said hollowed out portion of said second end.

19. An optical analyzer comprising:
A) a first electroptical transducer;
B) a second electroptical transducer, one of said transducers being a source and the other being a detector of a wavelength of light to be used for optical analysis of a material; and,
C) a cylindrical rod adapted for immersion in the material to be analyzed having a first and a second end, a cylindrical surface therebetween, and a centrally disposed axis of symmetry intersecting said ends, said first end of said rod having two end surfaces meeting at an angle having a first pair of legs at the intersection thereof with a plane coincident with said axis, said angle being slightly greater than twice the critical angle of incidence at said cylindrical surface of said rod when immersed in the material to be analyzed at said wavelength, said first transducer being located substantially on one of said end surfaces on a perpendicular bisector of one of said legs, and said second transducer being located at the other end of said rod.

20. The analyzer defined in claim 19; and,
D) a third optical transducer being located substantially on the other of said end surfaces on a perpendicular bisector of the other of said legs and wherein said first and said third transducer are light detectors and said second transducer is a light source.

* * * * *